(12) United States Patent
Fan et al.

(10) Patent No.: US 10,893,839 B2
(45) Date of Patent: Jan. 19, 2021

(54) COMPUTED TOMOGRAPHY SYSTEM AND METHOD CONFIGURED TO IMAGE AT DIFFERENT ENERGY LEVELS AND FOCAL SPOT POSITIONS

(71) Applicant: General Electric Company, Schenectady, NY (US)

(72) Inventors: Jiahua Fan, New Berlin, WI (US); Yannan Jin, Niskayuna, NY (US); Ming Yan, Hartland, WI (US); Uwe Wiedmann, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 181 days.

(21) Appl. No.: 16/001,289

(22) Filed: Jun. 6, 2018

(65) Prior Publication Data

US 2019/0374174 A1    Dec. 12, 2019

(51) Int. Cl.
| | | |
|---|---|---|
| A61B 6/03 | (2006.01) |
| A61B 6/00 | (2006.01) |
| G06T 7/00 | (2017.01) |
| G06T 11/00 | (2006.01) |

(52) U.S. Cl.
CPC ............ *A61B 6/032* (2013.01); *A61B 6/4028* (2013.01); *A61B 6/4411* (2013.01); *A61B 6/482* (2013.01); *G06T 7/0012* (2013.01); *G06T 11/005* (2013.01); *G06T 11/006* (2013.01); *G06T 2207/10081* (2013.01)

(58) Field of Classification Search
CPC .............................. A61B 6/032; A61B 6/4021
See application file for complete search history.

(56) References Cited

U.S. PATENT DOCUMENTS

| | | | |
|---|---|---|---|
| 7,236,559 B2 | 6/2007 | Jha et al. |
| 7,792,241 B2 | 9/2010 | Wu et al. |
| 7,813,474 B2 | 10/2010 | Wu et al. |
| 7,826,587 B1 | 11/2010 | Langan et al. |
| 7,844,030 B2 | 11/2010 | Wilson et al. |

(Continued)

FOREIGN PATENT DOCUMENTS

| | | |
|---|---|---|
| JP | 2009082173 | 4/2009 |
| JP | 2009082173 A | 4/2009 |

OTHER PUBLICATIONS

Machine Translation of JP 2009082173 (Year: 2009).*

(Continued)

*Primary Examiner* — Yara B Green

(57) ABSTRACT

A computed tomography (CT) imaging system and method, wherein the system includes an x-ray source that is operable to emit a beam of x-rays from a focal spot and move a spot position of the focal spot. The system also includes a detector assembly that is configured to detect the x-rays attenuated by the object. At least one processing unit is configured to execute programmed instructions stored in memory. The at least one processing unit is configured to direct the x-ray source to emit different beams of the x-rays at different energy levels and to receive data from the detector assembly that are representative of detection of the x-rays emitted at the different energy levels. The at least one processing unit is also configured to direct the x-ray source to move the focal spot such that the focal spot is at different spot positions while the different beams are emitted.

16 Claims, 10 Drawing Sheets

(56) References Cited

U.S. PATENT DOCUMENTS

| | | |
|---|---|---|
| 8,295,442 B2 | 10/2012 | Caiafa et al. |
| 8,363,917 B2 | 1/2013 | Fan et al. |
| 8,401,151 B2 | 3/2013 | Frontera et al. |
| 8,548,118 B2 | 10/2013 | Hsieh et al. |
| 8,712,015 B2 | 4/2014 | Caiafa |
| 8,861,681 B2 | 10/2014 | Caiafa et al. |
| 9,070,181 B2 | 6/2015 | Wu et al. |
| 9,135,728 B2 | 9/2015 | Fan et al. |
| 9,160,325 B2 | 10/2015 | Caiafa |
| 9,198,629 B2 | 12/2015 | Wiedmann et al. |
| 9,438,120 B2 | 9/2016 | Caiafa et al. |
| 9,504,135 B2 | 11/2016 | Caiafa et al. |
| 9,585,626 B2 | 3/2017 | Gao et al. |
| 2008/0247504 A1 | 10/2008 | Edic |
| 2012/0163530 A1 | 6/2012 | Sainath |
| 2013/0266115 A1* | 10/2013 | Fan .......................... A61B 6/06 378/16 |
| 2014/0105361 A1 | 4/2014 | Vogtmeier |
| 2014/0177794 A1 | 6/2014 | De Man et al. |
| 2015/0182179 A1 | 7/2015 | Edic |
| 2016/0106386 A1* | 4/2016 | Fan .......................... A61B 6/482 378/5 |

OTHER PUBLICATIONS

Marin et al. "State of the Art: Dual-Energy CT of the Abdomen" Radiology: vol. 271: No. 2; 2014 (16 pages).

Slavic et al. "GSI Xtream on Revolution CT" GE Healthcare; 2017 (20 pages).

Coursey et al. "Dual-Energy Multidetector CT: How does it work, What can it tell us, and When can we use it in Abdominopelvic Imaging" RadioGraphics; 2010 (17 pages).

Zhu et al. "Feasibility Study of Using Gemstone Spectral Imaging (GSI) and Adaptive Statistical Iterative Reconstruction (ASIR) for Reducing Radiation and Iodine Contrast Dose in Abdominal CT Patients with High BMI Values" PLOS One; 2015 (12 pages).

European patent application #19178545.0 filed Jun. 5, 2019; Search Report dated Oct. 16, 2019; 6 pages.

* cited by examiner

COMPUTED TOMOGRAPHY SYSTEM AND METHOD CONFIGURED TO IMAGE AT DIFFERENT ENERGY LEVELS AND FOCAL SPOT POSITIONS

FIELD

The subject matter disclosed herein relates generally to computed tomography medical imaging systems.

BACKGROUND

Computed tomography (CT) imaging systems (hereinafter CT systems) typically include an x-ray source that emits a fan-shaped or cone-shaped beam toward an object, such as a person or an inanimate object (e.g., luggage). The beam is attenuated by the object and impinges upon an array of detector cells. The intensity of the beam received at the detector array is typically dependent upon the attenuation of the x-ray beam by the object. Each detector cell of the detector array produces a separate analog signal indicative of the attenuated beam received by each detector cell. The analog signals are converted to digital signals and transmitted to an image-processing system for analysis.

The x-ray source and the detector array are rotated about the gantry within an imaging plane and around the subject. X-ray sources typically include x-ray tubes, which emit the x-ray beam from a focal point. X-ray detectors typically include an anti-scatter grid or collimator for rejecting scattered x-rays at the detector, a scintillator for converting x-rays to light energy adjacent the collimator, and photodiodes for receiving the light energy from the adjacent scintillator and producing electrical signals therefrom. The x-ray source is supplied power through a power system. Optionally, a portion of the generator rotates with the x-ray source and the detector array about the object.

CT systems may be configured to operate in different scanning modes. In a multi-energy acquisition mode, for example, the x-ray source is supplied with different operating voltages (or energy levels). Various CT system configurations use a variable operating voltage of the x-ray source including: (1) acquisition of low-energy and high-energy projection data from two sequential scans of the object using different operating voltages of the x-ray tube, (2) acquisition of projection data utilizing rapid switching of the operating voltage of the x-ray tube to acquire low-energy and high-energy information for an alternating subset of projection views, or (3) concurrent acquisition of energy-sensitive information using multiple imaging systems with different operating voltages of the x-ray tube.

Although such multi-energy acquisition modes can provide images that enable material density differentiation, other acquisition modes with one more improved characteristics (e.g., image quality, resolution, or sampling) are generally desired.

BRIEF DESCRIPTION

In accordance with embodiments herein, a computed tomography (CT) imaging system is provided. The system comprises an x-ray source that is configured to be powered by a power system at different operating voltages. The x-ray source is operable to emit a beam of x-rays from a focal spot toward an object. The x-ray source is operable to move a spot position of the focal spot. A detector is configured to detect the x-rays attenuated by the object. At least one processing unit is configured to execute programmed instructions stored in memory. While executing the programmed instructions, the at least one processing unit is configured to direct the x-ray source to emit different beams of the x-rays at different energy levels and to receive data from the detector that are representative of detection of the x-rays emitted at the different energy levels. The at least one processing unit is also configured to direct the x-ray source to move the focal spot between different spot positions such that the focal spot is at different spot positions while the beams are emitted at the different energy levels.

The at least one processing unit may be configured to direct the x-ray source to, repeatedly, emit a first beam at a higher-energy level from a first spot position, move the focal spot toward a second spot position after emitting the first beam from the first spot position, emit a second beam at a lower-energy level from the second spot position, and move the focal spot toward the first spot position after emitting the second beam from the second spot position. The beams may be emitted along an XY plane that may be perpendicular to a Z axis. The x-ray source may move the focal spot relative to the Z axis and relative to the XY plane. The x-ray source may include electrodes that may be spaced apart and positioned such that the beams of the x-rays may pass between the electrodes. The electrodes may be operable to adjust a strength of the electric field to move the spot position of the focal spot.

Optionally, the electrodes may be configured to move the spot position between first and second spot positions. The electric field may be operable to deflect the different beams by differing amounts. The x-ray source may include an electromagnet configured to generate a magnetic field. The electromagnet may be operable to adjust a strength of the magnetic field to move the spot position of the focal spot.

In some aspects, the at least one processing unit may be configured to receive higher-energy data from the detector while the focal spot is in a first position and may be configured to receive lower-energy data while the focal spot is in a second position. The at least one processing unit may be configured to interpolate the higher-energy data at the second position and the lower-energy data at the first position.

Optionally, the at least one processing unit is configured to generate material density projections for two different materials for the first position of the focal spot using (a) a material decomposition process and (b) the lower-energy data for the first position of the focal spot and the higher-energy data for the first position of the focal spot. The at least one processing unit may be configured to generate material density projections for the two different materials for the second position of the focal spot using (a) the material decomposition process and (b) the lower-energy data for the second position and the higher-energy data for the second position. After generating the material density projections for the two different materials from the first and second positions, the at least one processing unit may be configured to reconstruct high-resolution material-density images using the material density projections for the two different materials from the first and second positions.

Optionally, the at least one processing unit may be configured to generate higher-energy high-resolution images using the higher-energy data for the first focal position and the higher-energy data for the second focal position. The at least one processing unit may be configured to generate lower-energy high-resolution images using the lower-energy data for the first focal position and the lower-energy data for the second focal position. The at least one processing unit may be configured to then reconstruct high-resolution material-density images using the higher-energy and lower-energy high-resolution images.

In accordance with embodiments herein, a method is provided. The method directs an x-ray source to emit different beams of x-rays at different energy levels and directs the x-ray source to move a focal spot of the x-ray source between different spot positions such that the focal spot is at different spot positions while the beams are emitted at the different energy levels. The method receives data that is representative of detection of the x-rays emitted at the different energy levels.

Optionally, the method may direct the x-ray source to emit the different beams and to move the focal spot includes directing the x-ray source to repeatedly emit a first beam at a first energy level while the focal spot is in the first spot position, move the focal spot toward a different second spot position, emit a second beam having a different second energy level while the focal spot is in the second spot position and move the focal spot toward the first spot position. The beams may be emitted along an XY plane that may be perpendicular to a Z axis. The x-ray source may move the focal spot relative to the Z axis and relative to the XY plane while moving the focal spot between the different spot positions.

Optionally, the x-ray source may include electrodes that may be spaced apart and positioned such that the beams of the x-rays pass between the electrodes. Moving the focal spot may include adjusting a strength of an electric field between the electrodes. Adjusting the strength of the electric field may cause the different beams to be deflected by differing amounts. The x-ray source may include an electromagnet that may be configured to generate a magnetic field. Moving the focal spot may include adjusting a strength of a magnetic field of the electromagnet. Detecting the x-rays may include detecting higher-energy data and detecting lower-energy data. The method may further comprise interpolating the higher-energy data and interpolating the lower-energy data.

In accordance with embodiments herein, a computed tomography (CT) imaging system is provided. An x-ray source is configured to be powered by a power system at different operating voltages. The x-ray source is operable to emit a beam of x-rays from a focal spot toward an object. The x-ray source is operable to move a spot position of the focal spot. A detector is configured to detect the x-rays attenuated by the object. At least one processing unit is configured to execute programmed instructions stored in memory. The at least one processing unit, while executing the programmed instructions, is configured to direct the x-ray source to, repeatedly emit a first beam at a higher-energy level from a first spot position, move the focal spot toward a second spot position after emitting the first beam from the first spot position, emit a second beam at a lower-energy level from the second spot position and move the focal spot toward the first spot position after emitting the second beam from the second spot position.

Optionally, the beams may be emitted along an XY plane that may be perpendicular to a Z axis. The x-ray source may move the focal spot relative to the Z axis and relative to the XY plane. The x-ray source may include electrodes that may be spaced apart and may be positioned such that the beams of the x-rays pass between the electrodes. The electrodes may be operable to adjust a strength of the electric field to move the spot position of the focal spot.

The detector may include a plurality of detector pixel elements in which each detector pixel element of said plurality may detect the x-rays emitted at higher energy levels and the x-rays emitted at lower energy levels.

BRIEF DESCRIPTION OF THE DRAWINGS

The inventive subject matter described herein will be better understood from reading the following description of non-limiting embodiments, with reference to the attached drawings, wherein below.

DETAILED DESCRIPTION

Figure 1:
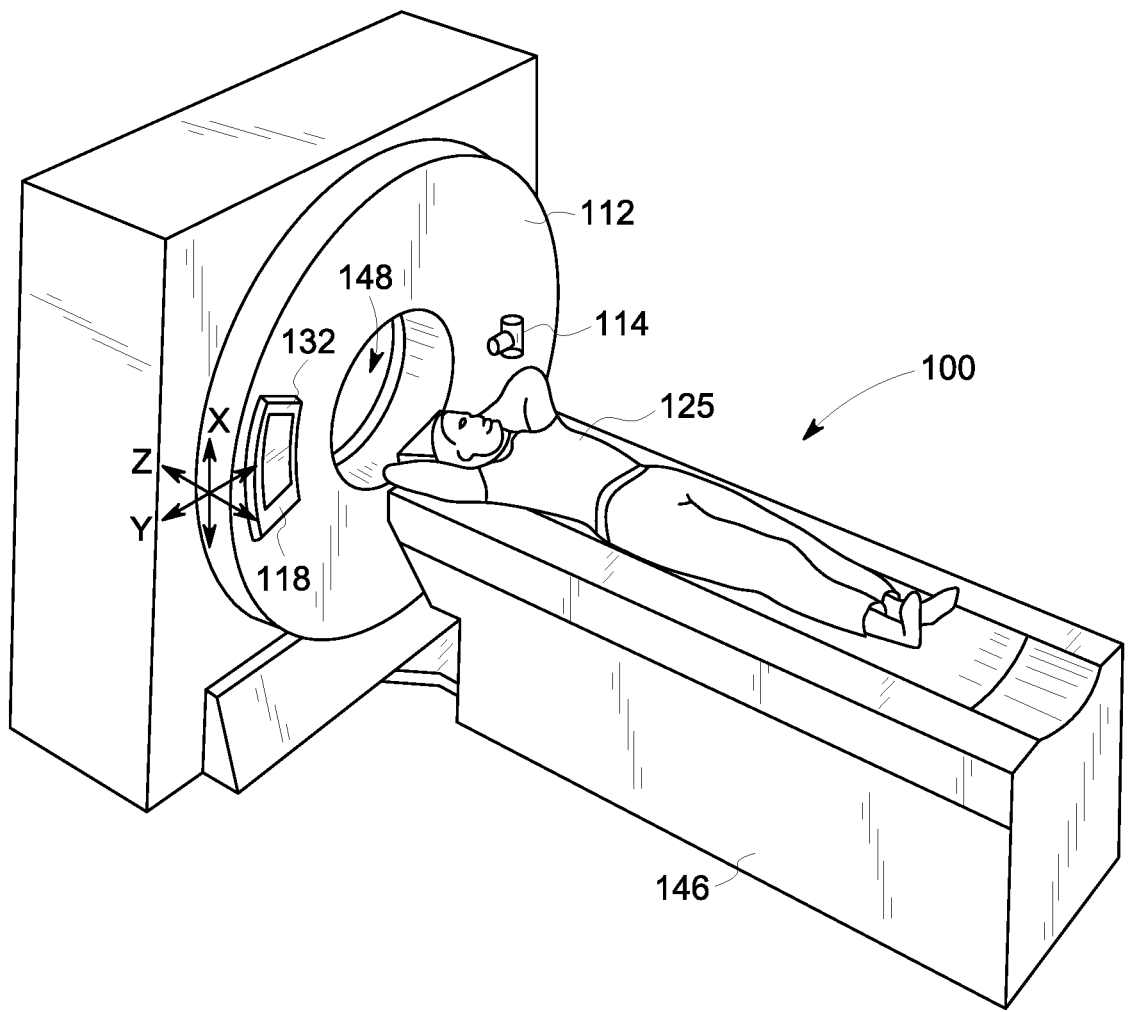
FIG. 1 illustrates a computed tomography (CT) system in accordance with one embodiment.

Embodiments set forth herein may increase spatial sampling in a CT imaging system by dynamically adjusting a position of a focal spot of the imaging system with respect to a detector assembly of the imaging system. Image data acquired from different locations of the focal spot may be interlaced together to form higher sampling data (relative to the image data acquired with a single focal spot position) before going through an image reconstruction process. As described herein, the CT system also can acquire image data at different energy levels. For example, the CT system may use fast kV switching in which a generator of the imaging system oscillates an energy level supplied to an x-ray source. This allows for both spectral information and high-resolution sampling to be achieved concurrently as the x-ray source and the detector assembly are moved relative to a body being imaged by the imaging system.

As used herein, the terms "high energy" and "low energy" do not require specific values or ranges. Instead, the terms "high" and "low" are labels that identify an energy level relative to another energy level. For example, a high-energy level has an energy that is greater than a low-energy level, and the low-energy level has an energy that is less than the high-energy level. The high-energy and low-energy levels may be, for example, 140 kV and 80 kV, respectively. Optionally, high-energy levels can be energy levels above or in excess of 80 kV, while low-energy levels may be energy levels that are no greater than 80 kV.

Embodiments set forth herein are described with respect to a multi-slice CT system capable of spectral imaging in which the CT system acquires data sets at different energy levels. For example, the CT system may be configured to cycle or switch energy (kV) from high to low at a switching rate (e.g., up to 4.8 kHz) and utilize the detector assembly to capture two data sets that are temporally registered. In some embodiments, the beam energy is non-static such that the beam energy cycles in a sinusoidal manner during image acquisition. As such, energy levels may be characterized as a mean-high energy level and a mean-low energy level. The mean-high energy level may have, for example, a maximum of about 140 kV, and the mean-low energy level may have a minimum of about 80 kV.

CT systems set forth herein may also be configured to dynamically control a position of a focal spot of the x-ray beam during data acquisition. For example, the focal spot may move between a first position and a second position as the x-ray source and the detector move relative to the person (e.g., helically or axially). A sample is acquired while the focal spot is at the first focal position, and another sample is acquired while the focal spot is at the second focal position. The different focal positions effectively provide different view angles or beam orientations with respect to the detector assembly. The position of the focal spot may be dynamically controlled through electrostatic deflection of the beam and/or magnetic deflection of the beam.

In some embodiments, an x-ray source may emit a first beam at a first energy level while the focal spot is in the first spot position and emit a second beam having a different second energy level while the focal spot is in the second spot position. It should be understood that the phrase "while the focal spot is in [a designated] spot position" does not require that the focal spot be completely stationary as the beam is emitted or that the energy level be uniform throughout emission. The focal spot may be constantly moving and the energy level may be constantly changing. However, the amount of movement and/or the amount of change in energy during emission may be relatively small or may offset one another such that useful data may be acquired for generating image data at different energy levels and/or from different focal spots. For example, the average spot position during emission of the first beam and the average spot position during emission of the second beam may be sufficiently spaced apart such that useful data (e.g., data representing samples from different spot positions) may be obtained. Likewise, the average energy level during emission of the first beam and the average energy level during emission of the second beam may be sufficiently different such that useful data (e.g., data representing samples from different energy levels) may be obtained.

The CT system may be configured for axial scanning, helical scanning, and cine scanning. Embodiments can also be used to detect, measure, and characterize materials that may be injected into the subject such as contrast agents and other specialized materials using energy weighting to boost the contrast of iodine and calcium (and other high atomic or materials). Contrast agents can, for example, include iodine that is injected into the blood stream for better visualization. For baggage scanning, the effective atomic number generated from energy sensitive CT principles allows reduction in image artifacts, such as beam hardening, as well as provides addition discriminatory information for false alarm reduction.

In some embodiments, at least one technical effect of the subject matter described herein includes the ability to generate spectral image data that has a higher spatial resolution with fewer aliasing artifacts compared to spectral image data generated by some known systems. In some embodiments, at least one technical effect of the subject matter described herein includes the ability to generate high-resolution image data having an improved overall image quality compared to high-resolution image data generated by known systems. In some embodiments, at least one technical effect of the subject matter described herein includes enabling a spectral imaging mode for clinical applications that have heretofore not used spectral imaging (e.g., due to a lack of spatial resolution).

Figure 2:
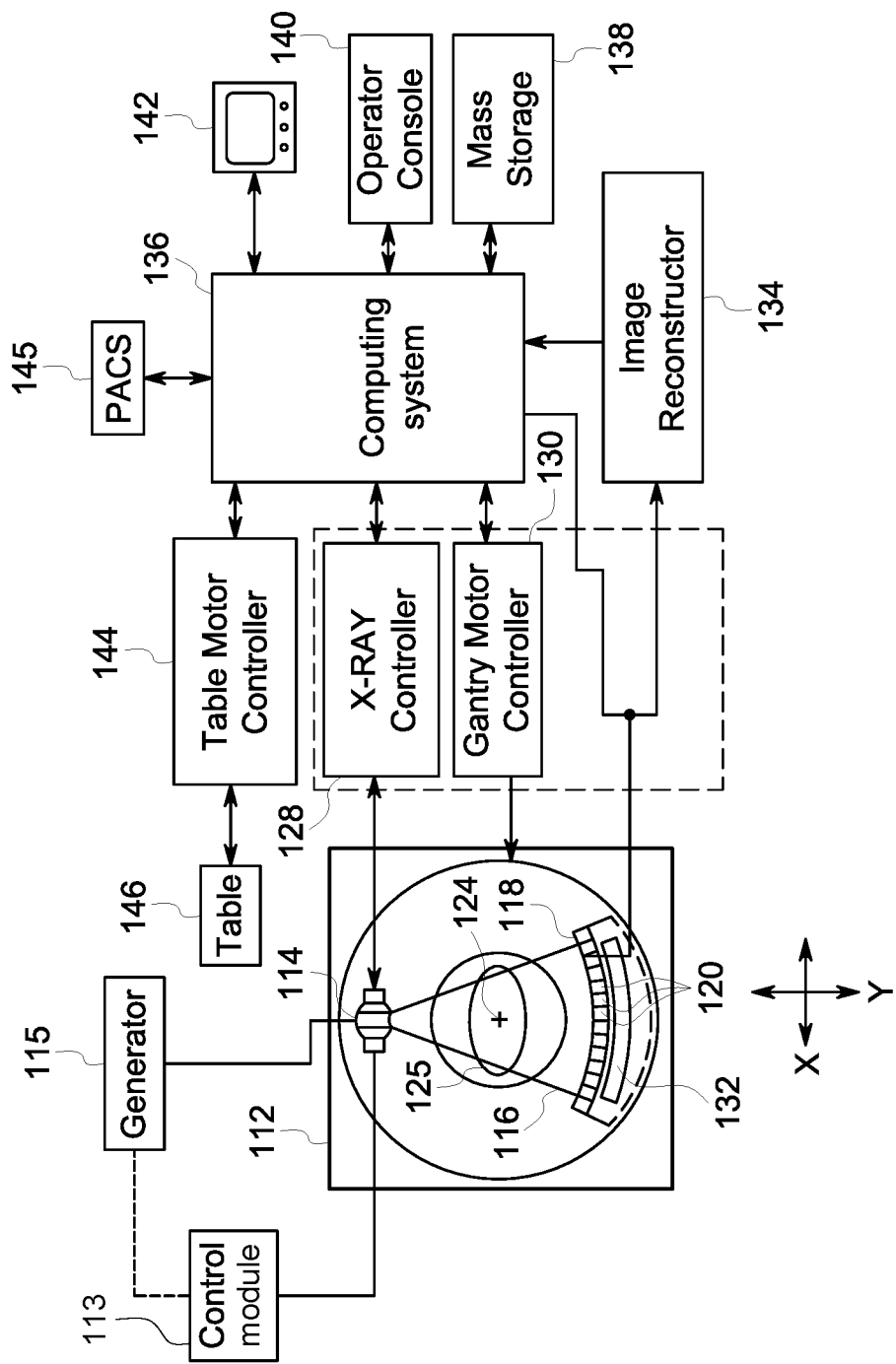
FIG. 2 is a schematic diagram of the CT system of FIG. 1.

FIG. 1 illustrates a computed tomography (CT) imaging system 100 (referred to herein as a CT system), and FIG. 2 illustrates a schematic diagram of the CT system 100. As shown, the CT system 100 includes a gantry 112 having an x-ray source 114 (e.g., x-ray tube) that projects a beam of x-rays toward an opposing detector assembly 118 of the gantry 112. Optionally, the gantry 112 and the components mounted thereon may rotate about a center of rotation 124 during a scan. In some embodiments, the detector assembly 118 may include a layer for conversion of x-ray to light (e.g., scintillator layer), a layer for converting light to current (e.g., photodiode layer), and a substrate layer to support electronics for communicating data. The detector assembly 118 includes a plurality of detector cells or modules 120 and a data acquisition system (DAS) 132. Each detector cell 120 may include a group or array of pixel elements in which each pixel element is configured to sense x-rays. The plurality of detector cells 120 sense the projected x-rays 116, including those that pass through and are attenuated by an object or body 125. The detector cells 120 may communicate data that is representative of the detection of the x-rays by the detector cells 120 or, more specifically, the pixel elements of the respective detector cells 120. The object 125 is hereinafter referred to as a person, but it should be understood that the object may be, for example, luggage or another inanimate object.

FIGS. 1 and 2 illustrate a coordinate system relative to rotatable components of the gantry 112, such as the detector assembly 118 and the x-ray source 114. The x-ray source 114 is supplied power through a generator 115. In some embodiments, at least a portion of the generator 115 (e.g., second stage) rotates with the x-ray source 114. The coordinate system includes mutually perpendicular X, Y, and Z-axes. The Z-axis extends generally along an axial length of the person 125 and extends parallel to the axis of rotation 124. The Z-axis defines a slice direction of the CT system 100. The X- and Y-axes define a plane that is perpendicular to the Z-axis. The x-ray source 114 and the detector assembly 118 coincide with and face in a direction along the XY plane. The direction may be a vector that, depending upon the rotational orientation of the x-ray source 114 and the detector assembly 118, has an X component and a Y component. The generator 115, the x-ray source 114, and the detector assembly 118 may rotate circumferentially about the axis of rotation 124 (FIG. 2) as a group.

The generator 115 supplies the power and, optionally, timing signals to the x-ray source 114. The generator 115 may output a first voltage and output a second voltage to the x-ray source 114. In some embodiments, the first and second voltages may be outputted in a fast-switching pattern such that the voltage increases and decreases in a sinusoidal manner between a maximum first voltage and a minimum second voltage (e.g., 140 kVp and 80 kVp). Optionally, the generator 115 may cause the first voltage and the second voltage to be effectively switched at a frequency of up to 2 kHz or more. In other embodiments, the generator 115 causes the first voltage and the second voltage to be switched at frequencies of 550 Hz or more. By rapidly switching the voltage supplied to the x-ray source 114, samples may be obtained at low energy levels (80 kVp) and high energy levels (140 kVp).

Operation of the x-ray source 114 may be controlled, in part, by a deflection-control module 113. The deflection-control module 113 is configured to control an electrical and/or magnetic field that deflects electrons from the x-ray source 114 prior to the electrons reaching a focal spot from which the beam 215 projects. As described herein, the deflection-control module 113 may control an electrical field formed by electrodes or may control a magnetic field formed by an electromagnet (e.g., solenoid). More specifically, the deflection-control module 113 may increase or decrease a strength of the respective field, thereby increasing or decreasing an amount of deflection. Optionally, the deflection-control module 113 is operably coupled to the generator 115 such that a change in power level causes a change in a strength of the respective field.

The deflection-control module 113 may form part of the at least one processing unit that controls operation of the CT system. For example, the deflection-control module 113 may form part of the computing system 136 and/or part of the x-ray controller. Alternatively, at least a portion of the deflection-control module may be separate circuitry (e.g., hardwired electronics) that directly connects the voltage source and the x-ray source.

In certain embodiments, the CT system 100 is configured to traverse different angular positions around the person 125 for acquiring desired projection data. Accordingly, the gantry 112 and the components mounted thereon may be configured to rotate about a center of rotation 124 for acquiring the projection data. The table 146 may be moved along the axis of rotation 124 as the gantry 112 is rotated or, alternatively, as the gantry 112 remains in a fixed position.

The detector cells 120 may communicate data that is representative of the detection of the x-rays by the pixel elements. For example, each detector cell 120 may communicate an analog electrical signal that represents the intensity of impinging x-rays attenuated by the person 125. The detector cells 120 provide the analog electrical signals (or data) to the DAS 132. The DAS 132 samples the analog data received from the detector cells 120 and converts the analog data to digital signals (or digital data) for subsequent processing. The DAS 132 may communicate the data that is representative of the detection of the x-rays to a computing system 136.

The computing system 136 may include or be represented by at least one processing unit. For example, the computing system 136 may include multiple processing units (e.g., a combination of processors, hardwired circuitry, or other logic-based devices) distributed throughout the CT system 100. The at least one processing unit, which may be referred to generally as 136, is configured to execute programmed instructions stored in memory 138. While executing the programmed instructions, the at least one processing unit is configured to control operation of the x-ray source 114 and the generator 115, among other things.

In one example, the computing system 136 stores the data in a memory 138, which is labeled as a "storage device" in FIG. 2. The memory 138, for example, may include a hard disk drive, a floppy disk drive, a compact disk-read/write (CD-R/W) drive, a Digital Versatile Disc (DVD) drive, a flash drive, and/or a solid-state storage device. The computing system 136 may also process the data to generate images.

Additionally, the computing system 136 provides commands and parameters to one or more of the DAS 132, the x-ray controller 128, and the gantry-motor controller 130 for controlling system operations. In certain embodiments, the computing system 136 controls system operations based on operator input. Although FIG. 2 illustrates only one operator console 140, more than one operator console may be coupled to the CT system 100, for example, for inputting or outputting system parameters, requesting examinations, and/or viewing images. Further, in certain embodiments, the CT system may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the CT system 100 either includes, or is coupled to, a picture archiving and communications system (PACS) 145. In one example implementation, the PACS 145 is further coupled to a remote system, such as a radiology department information system, hospital information system, or an internal or external network (e.g., cloud-computing network). The remote system allows operators at different locations to supply commands and parameters and/or gain access to the image data. In particular embodiments, the remote system enables users to retrieve, update, and store designated protocols.

The computing system 136 uses the operator-supplied and/or system-defined commands and parameters to operate a table motor controller 144, which in turn, may control a motorized table 146. Particularly, the table motor controller 144 moves the table 146 to appropriately position the person 122 in the gantry 112 for acquiring projection data corresponding to the target volume of the person 122.

As described above, the DAS 132 samples and digitizes the projection data acquired by the detector cells 120. Subsequently, an image reconstructor 134 uses the sampled and digitized x-ray data to perform high-speed reconstruction. Although FIG. 2 illustrates the image reconstructor 134 as a separate entity, in certain embodiments, the image reconstructor 134 may form part of the computing system 136. Alternatively, the image reconstructor 134 may be located locally or remotely, and may be operatively connected to the CT system 100 using a wired or wireless network. Particularly, one exemplary embodiment may use computing resources in a cloud-computing network for the image reconstructor 134.

In one embodiment, the image reconstructor 134 reconstructs the images stored in the storage device 138. Alternatively, the image reconstructor 134 transmits the reconstructed images to the computing system 136 for generating useful person information for diagnosis and evaluation. In certain embodiments, the computing system 136 transmits the reconstructed images and/or the person information to the display 142 communicatively coupled to the computing system 136 and/or the image reconstructor 134.

The various methods and processes described further herein may be stored as executable instructions in non-transitory memory in the CT system 100. For example, the computing system 136, the x-ray controller 128, the detector assembly 118, the table-motor controller 144, and the gantry-motor controller 130 may include instructions in non-transitory memory, and may apply the methods described herein to scan the person 125.

As used herein, the phrase "at least one processing unit" or the phrase "the computing system" includes the possibility of multiple processing units (e.g., processors, hardwired circuitry, or other logic-based devices) distributed throughout the CT system 100. For example, the phrase "at least one processing unit" may include a combination of one or more processing units of the computing system 136, one or more processing units of the x-ray controller 128, and one or more processing units of the gantry-motor controller 130, one or more processing units of the table-motor controller 128, and one or more processing units of the image reconstructor 134. The at least one processing unit may executed programmed instructions stored in memory to direct components of the CT imaging system to operate as described herein. For example, the at least one processing unit may direct the x-ray source, the detector, or the generator to operate as set forth herein. The at least one processing unit may also process (e.g., reconstruct) the data acquired during the CT scan to generate image data.

The computing system 136 also receives commands and scanning parameters from an operator via console 140 that has an operator interface. The operator interface may include, for example, a keyboard, mouse, voice-activated controller, touch-sensitive screen or pad, or any other suitable input apparatus. An associated display 142 allows the operator to observe the reconstructed image and other data from computing system 136. Optionally, the display 142 forms part of the operator interface and includes a touch-sensitive screen.

Optionally, a filter (not shown) may be positioned between the person 125 and the x-ray source 114. For example, bowtie filters may be used to modulate the output of the radiation source. Bowtie filters can compensate for the difference in beam path length through the axial plane of the object such that a more uniform fluence can be delivered to the detector. Bowtie filters can also reduce scatter and radiation dosage at the periphery of the imaging field of view (FOV).

As described herein, embodiments of the subject matter are capable of acquiring data sets at different energy levels. For example, the CT system may be configured to cycle or switch energy (kV) from high to low and utilize the detector assembly to capture two data sets that are temporally registered. A previously proposed design for acquiring data sets having different energy levels included positioning a grating collimator between the person and the x-ray tube. If the bowtie filter was used, the grating collimator could be positioned on either side of a bowtie filter. The proposed grating collimator included alternating regions in which each region has the same material (e.g., air and tungsten), which differs from the material of the other region. The different materials have a different attenuation of the x-rays. In particular embodiments, the CT system is devoid of a grating collimator that includes alternating regions in which at least one of these regions attenuates the x-rays prior to reaching the person.

As part of the previously proposed design, an alternating pattern of x-rays would be incident upon the detector. X-rays for either energy level (high or low) would be incident upon the pixel elements of the detector in an alternating manner. The x-ray source and the detector are designed to achieve the alternating pattern. In particular embodiments, the CT system is not designed to achieve an alternating pattern of incident x-rays on the detector surface and the x-rays are not attenuated based on energy level.

Figure 3:
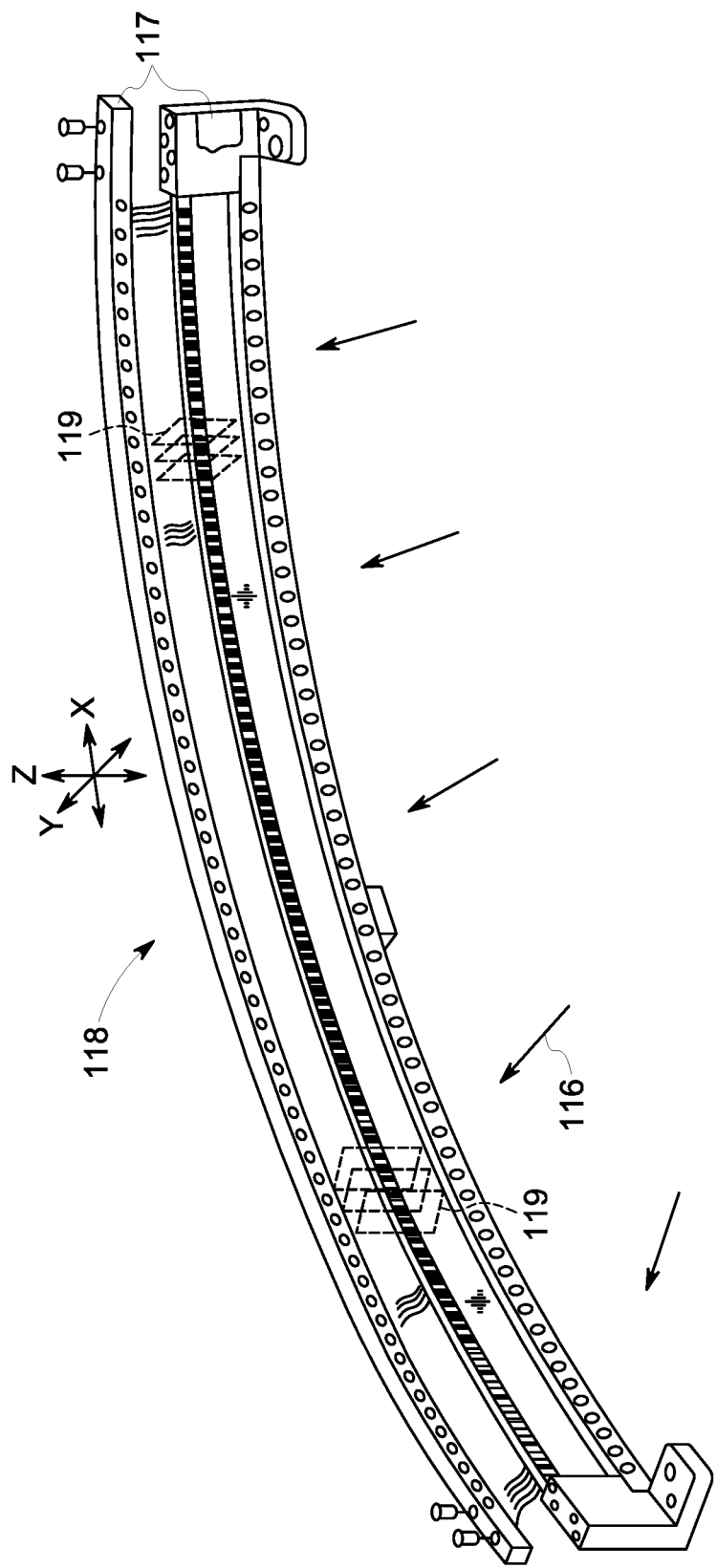
FIG. 3 illustrates a portion of a detector assembly that may be used with the CT system of FIG. 1.

FIG. 3 illustrates one embodiment of the detector assembly 118 in greater detail. It should be understood, however, that other embodiments may include detector assemblies with other designs and configurations. The detector assembly 118 includes rails 117 having collimating plates 119 placed therebetween. The collimating plates 119 are positioned to collimate x-rays 116 before the x-rays 116 impinge upon, for instance, the detector cells 120 (FIG. 2) of the detector assembly 118. Each of the detector cells 120 may include a number of detector pixel elements, which may be referred to as pixel elements, detector pixels, or detector elements. The detector pixel elements may be optically coupled to backlit diode array (not shown) that is, in turn, electrically coupled to the DAS 132 (FIG. 2). In operation, x-rays 116 pass through and are attenuated by the person 125 and then impinge upon the detector pixel elements of each detector cell 120, thereby generating an analog signal that is communicated to the DAS 132. The DAS 132 converts the analog signal to a digital signal.

As an example of one or more embodiments, the detector assembly 118 may include an array of collimating plates 119 that are positioned for fifty-seven detector cells 120 in which each of the detector cells 120 has 64×16 detector pixel elements. As such, the detector assembly 118 of FIG. 3 may have sixty-four rows and nine hundred twelve columns (sixteen by fifty-seven detector cells), which enables sixty four simultaneous slices of data to be collected with each rotation of the gantry 112 (FIG. 1).

During operation, multiple sets of measurements (or sets of attenuation data) may be acquired at different respective energy levels (e.g., mean energy levels) and at different focal spots. The measurements ($I_L$ and $I_H$) at two different energy spectra $S_L(E)$ and $S_H(E)$ can be given by:

$$I_L \int S_L(E) \exp(-\int \mu(r,E)dr)dE$$

$$I_H \int S_H(E) \exp(-\int \mu(r,E)dr)dE$$

where $\mu$ is the linear attenuation coefficient at energy E and location r.

Typically, the linear attenuation coefficient $\mu$ can be decomposed into two (or more) basis materials:

$$\mu(r,E) = a(r)A(E) + b(r)B(E)$$

where a(r) and b(r) are the spatially varying coefficient, and A(E) and B(E) are the energy dependencies of the respective basis materials.

Similarly, the line integral of the linear attenuation coefficient can be decomposed as:

$$\int \mu(r,E) = A(E) \int a(r) + B(E) \int b(r) = A(E)p_a + B(E)p_b$$

where $p_a$ and $p_b$ are the basis material line integrals.

The set of current measurements ($I_L$ and $I_H$) may thus be re-written as:

$$I_L = f_L(p_a, p_b)$$

$$I_H = f_H(p_a, p_b)$$

where the functions $f_L$ and $f_H$ can be determined empirically, based on calibration measurements of different material combinations with spectra $S_L$ and $S_H$, after which $p_a$ and $p_b$ can be computed.

In some embodiments, the inverse functions $g_a$ and $g_b$ may be directly defined from calibration experiments, resulting in the following material decomposition (MD) step:

$$p_a \cdot g_a(I_L, I_H)$$

$$p_b \cdot g_b(I_L, I_H)$$

A reconstruction algorithm may be used to reconstruct a(r) and b(r) based on sinograms $p_a$ and $p_b$, respectively. The reconstruction algorithm can be a direct algorithm (such as filtered backprojection) or an iterative algorithm (such as penalized weighted least squares with ordered subsets or iterative coordinate descent). In such cases, the input to the reconstruction algorithm are sinograms $p_a$ and $p_b$ obtained. In other embodiments, an iterative reconstruction process may be performed with unknowns a(r) and b(r) and using the measurements $I_L$ and $I_H$ as inputs. Embodiments may start from a first reconstruction of the basis materials and improve the reconstructed images by incorporating knowledge of the noise in the measurements and prior knowledge on the images.

Figure 4:
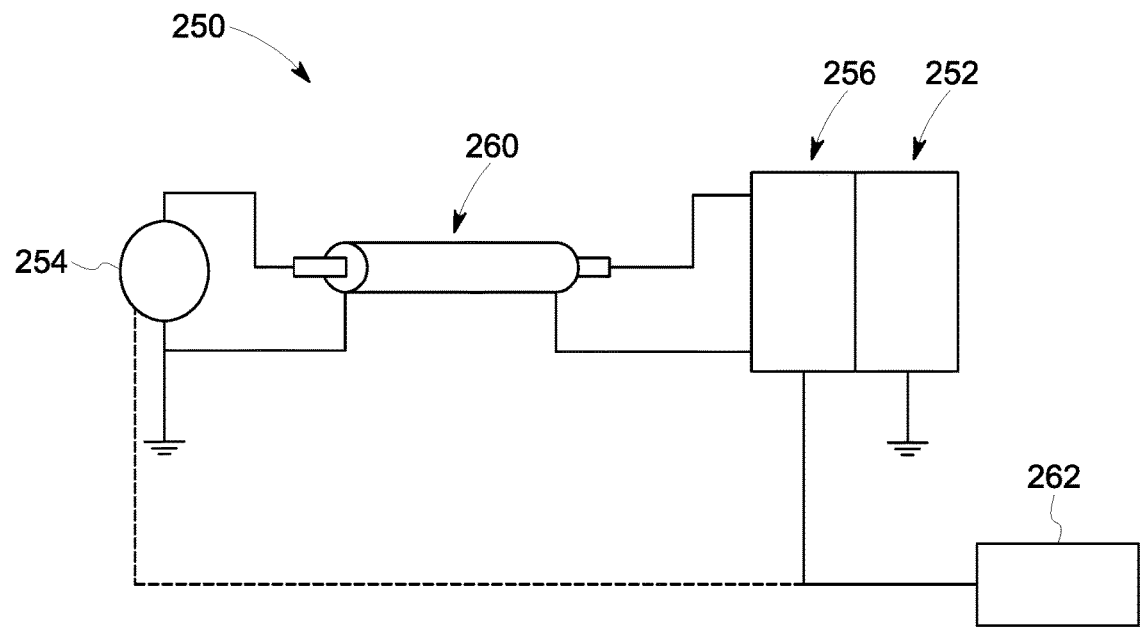
FIG. 4 is a schematic diagram of a power system in accordance with an embodiment that is configured to supply power to an x-ray source at different energy levels.

FIG. 4 is a schematic diagram of a power system 250 that is operable to supply power to an x-ray source 252. The power system 250 includes a voltage source 254 (e.g., high frequency, high voltage power generator). Optionally, the power system 250 includes an interposer circuit 256. The interposer circuit 256 is operable to rapidly switch or assist in switching between a first voltage level and a second voltage level. In some embodiments, the power system 250 is communicatively coupled to a deflection-control module 262. As described above, a deflection-control module may form a part of the computing system 136 and/or a part of the x-ray controller 128. In some embodiments, the deflection-control module 262 may be communicatively coupled to the interposer circuit 256 and/or communicatively coupled to the voltage source 254. In some embodiments, the deflection-control module 262 may be integrated with interposer circuit 256.

The interposer circuit 256 may include, for example, a voltage divider and a plurality of switching stages coupled in series. Each switching stage may have a pair of switches, a diode operable to block reverse current flow, and a capacitor. Under operation, the interposer circuit 256 may receive a voltage from a high-voltage generator, such as the voltage source 254. The series of switching stages enables rapid switching of the input voltage between a pair of voltage levels at an output. The total number of switching stages depends upon the magnitude of voltage increase.

The power system 250 is configured to supply an x-ray source 252 with electrical power at an operating voltage for generating an x-ray beam at a designated energy level. In some embodiments, the voltage source 254 and the interposer circuit 256 may be configured as an active resonant module. In some embodiments, the voltage source 254 and the interposer circuit 256 may be configured as a passive resonant module. The interposer circuit 256 may include switching component(s) that facilitate switching of the voltage generated from the voltage source 254 and applied to an X-ray tube 252. For example, in operation, the interposer circuit 256 provides switching between a high kV level (e.g., 140 kV) and a low kV level (e.g., 80 kV). However, it should be noted that other high and low voltage levels may be provided and the various embodiments are not limited to a particular voltage level. As another example, the high kV level can range from a few tens of kV (e.g., about 30 kV for mammography) to hundreds of kV (e.g., about 450 kV for industrial inspection applications). The energy may be reused and recirculated when switching between the voltage levels. In some embodiments, switching between the voltage levels can occur in about ten to one hundred microseconds or less.

In a resonant configuration of one or more embodiments, the electronics of the CT system can transmit power to the X-ray source 252 to charge or continue to provide power to the load (e.g., vacuum tube) at high voltage operation at different voltage levels. As shown, the interposer circuit 256 is secured to the x-ray source 252 and electrically coupled to the voltage source 254 through cabling 260. The cabling 260 may be rated for high voltages (e.g., 140 kV or more). In particular embodiments, the interposer circuit 256 may be integrated with the voltage source 254 such that the interposer circuit 256 forms part of the voltage source. In such embodiments, the voltage source 254 and the interposer circuit can be communicatively coupled to the x-ray source 252 through the cabling 260.

In particular embodiments, the voltage source 254 is a high voltage generator capable of generating voltages corresponding to low levels, for example, 80 kV, and the interposer circuit 256 is configured to provide additional energy/power to operate the load (e.g., vacuum chamber) at a high voltage level, for example, 140 kV. The interposer circuit 256 may operate to store energy when switching from a high voltage level to a low voltage level, and use the stored energy when transitioning to the next high voltage cycle. The interposer circuit 256 may store energy in, for example, one or more capacitors.

The deflection-control module 262 may be separate from or integrated with the interposer circuit 256. As described herein, the deflection-control module 262 is configured to dynamically control a position of the focal spot. In some embodiments, the deflection-control module 262 controls the position of the focal spot in response to a change in the power supplied to the x-ray source 252.

Figure 5:
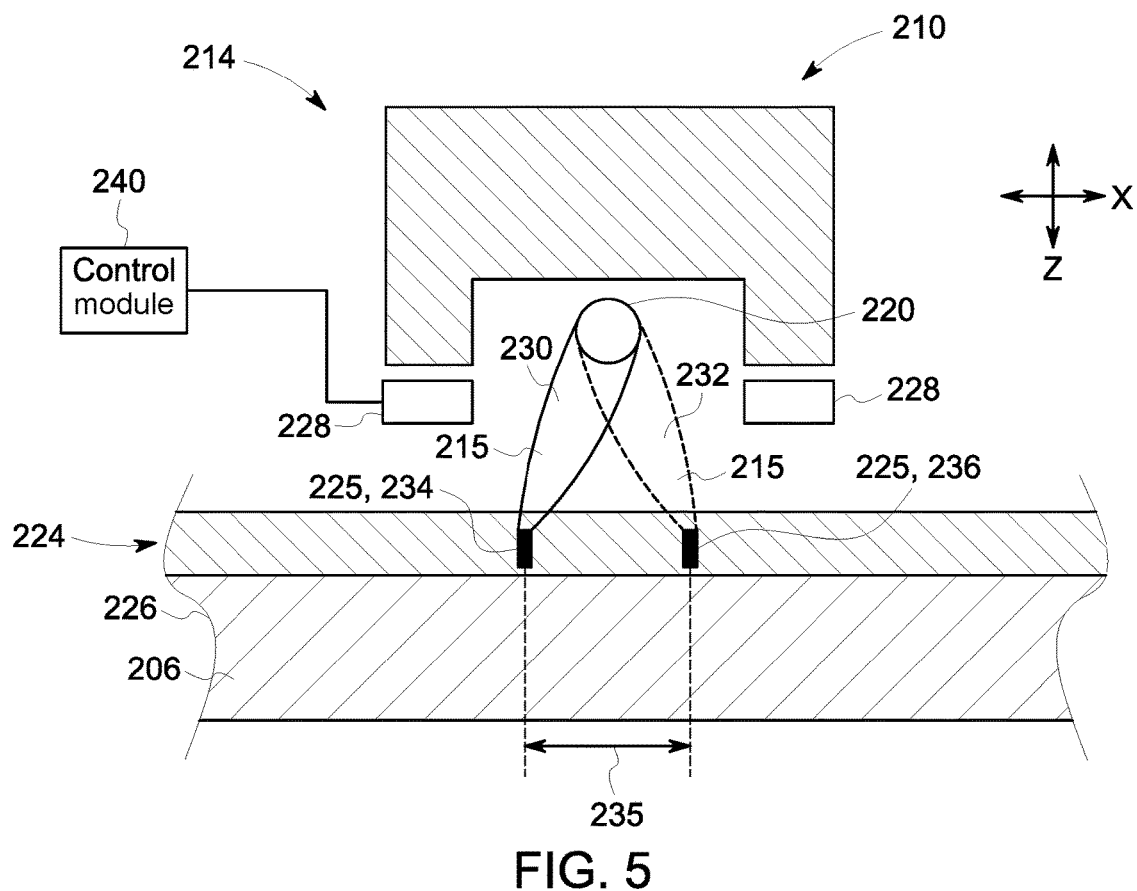
FIG. 5 is a side view of an x-ray source in accordance with an embodiment having a dynamic focal control mechanism that uses electrostatic deflection.

FIG. 5 is a schematic view of an x-ray source 214 illustrating one mechanism for dynamic focal spot control. The x-ray source 214 is configured to emit different beams at different energy levels. As shown, the x-ray source 214 includes a cathode 210 having a filament 220. A beam 215 of electrons is emitted from filament 220. The beam 215 may be directed to a focal spot 225 at a first focal position 234 on an anode 206, and the beam 215 may be directed to the focal spot 225 at a second focal position 236 on the anode 206. The anode 206 includes a beveled surface 224 positioned on a base 226 of the anode 206.

The beam 215 is electrostatically deflected by an electrode assembly having electrodes 228, 229 (e.g., electrode plates) as the electrons pass therethrough. Optionally, the x-ray source 214 may include additional electrodes to facilitate deflection, steering, or focusing the beam 215. The electrodes may be configured to deflect, steer, or focus the beam 215 in either direction along the page (as shown in FIG. 5) or in a perpendicular direction into and out of the page. The beam 215 of electrons may be directed along a path 230 to the focal spot 225 at the first focal position 234 or directed along a second path 232 to the focal spot 225 at the second focal position 236 by applying an electric field between the electrodes 228, 229. This electric field may change (in magnitude and/or direction) with respect to time. Accordingly, a beam of electrons emitted from a single filament 220 may be rapidly oscillated (or wobbled) between by varying the electrostatic field. A distance 235 exists between the first and second focal positions 234, 236.

In some embodiments, the beam 215 may oscillate the distance 235 along a path in the XY plane, wherein the path is generally transverse to the beam direction. In other embodiments, the beam 215 may oscillate the distance 235 along a path that extends along the Z-axis. The beam 215 may oscillate up to several kHz or more. For example, the beam may oscillate at approximately 5 kHz. As such, x-rays can be caused to emit from the first and second focal positions 234, 236 such that a beam 215 is projected toward the detector assembly 118 (FIG. 1).

In addition to moving the focal spot 225 between the first and second positions 234, 236, the x-ray controller 128

(FIG. 2) may cause the energy level to change. For example, the x-ray controller 128 may cause the energy level to change by fast kV switching.

Also shown, the x-ray source 214 may include or be controlled by a deflection-control module 240 that is operably coupled to the electrodes 228, 229. The deflection-control module 240 may control a potential difference between the pair of electrodes 228, 229 so that the different beams may be deflected by differing amounts. As the electrons pass between the electrodes 228, 229, the electrons are deflected. The amount of deflection is a function of the strength of the electric field, which is determined by the deflection-control module 240.

When the focal positions are controlled electrostatically using, for example, the mechanism shown in FIG. 5, the deflection is approximately proportional to 1/kV. Optionally, the deflection-control module 240 may be communicatively coupled to the generator, such as the generator 115, such that the strength of the electric field between the electrodes 228, 229 changes with a change in the power level supplied to the x-ray source. It is noted that for any given electric field, both a high energy level (e.g., 140 kVp) beam and a low energy level (e.g., 80 kVp) beam will be deflected in a common direction, but the high energy level beam will be deflected more than the low energy level beam. For example, a lower-energy beam may be deflected by a first amount, and the higher-energy beam may be deflected by a second amount that is greater than the first amount.

Optionally, the position of the focal spot and the energy level of the electron beam may be synchronized. For example, the generator may be directly connected to the electrodes (e.g., hardwired) and function as the deflection-control module. In such embodiments, the generator may independently and quickly switch the voltages applied to the deflection electrodes 228, 229.

Figure 6:
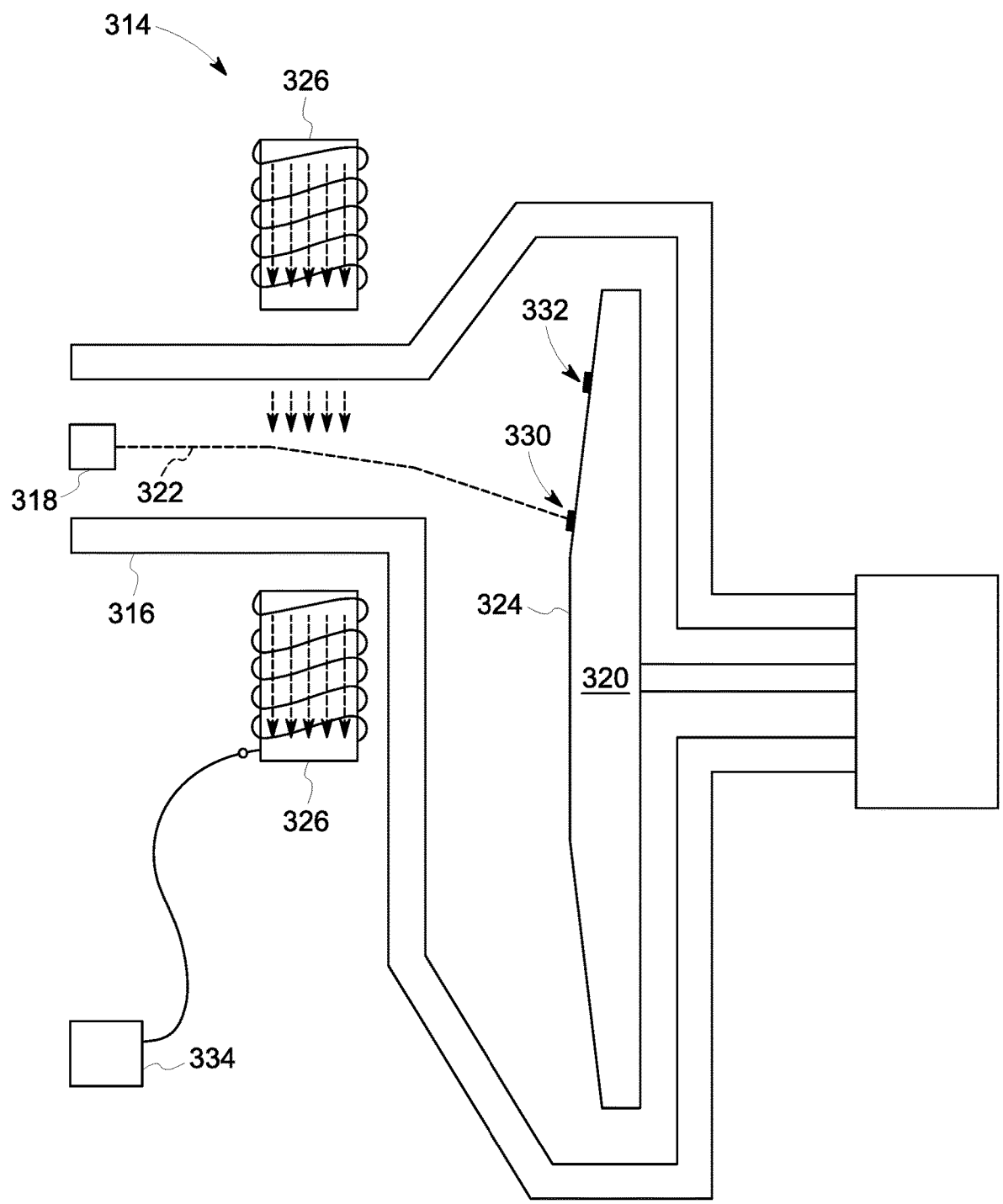
FIG. 6 is a side view of an x-ray source in accordance with an embodiment having a dynamic focal control mechanism that uses magnetic deflection.

FIG. 6 illustrates a cross-sectional view of an x-ray source 314 according to an embodiment that is configured to emit different beams at different energy levels. The x-ray source 314 includes a vacuum chamber or frame 316 having a cathode assembly 318 and a target or rotating anode 320 positioned therein. The cathode assembly 318 includes several elements, including a cathode cup (not shown) that supports a filament (not shown) and serves as an electrostatic lens that focuses a beam 322 of electrons emitted from the heated filament toward a surface 324 of the target 320.

An electromagnet assembly 326 (e.g., deflection coil) of the x-ray source 314 is mounted at a location near the path of the electron beam 322. According to one embodiment, the electromagnet assembly 326 may include a coil that is wound as a solenoid and is positioned over and around vacuum chamber 316 such that the magnetic field created is in the path of electron beam 322. The electromagnet assembly 326 generates a magnetic field that acts on electron beam 322, causing the electron beam 322 to deflect and move between a pair of focal spots or positions 330, 332. The direction of movement of the electron beam 322 is determined by the direction of current flow though coil of the electromagnet assembly 326.

In some embodiments, the electromagnetic assembly 326 includes one or more quadrupoles or a plurality of dipoles. For example, the electromagnet assembly 326 may include two sets of quadrupole coils and yokes in which the yokes of each are distributed around the path of the beam. The quadrupoles may be configured for focusing, and the dipoles may be configured for deflection. However, the quadrupoles may have second-order effects with respect to deflection, and the dipoles may have second-order effects with respect to focusing.

A direction and magnitude of current flow may be controlled via a deflection-control module 334 that is coupled to electromagnet 326. The deflection-control module 334 may be hardwired circuitry that is controlled by, for example, the x-ray controller 128 (FIG. 2) and/or the power system. The deflection-control module 334 may include a current source (e.g., real current source or ideal current source), voltage sources (e.g., low voltage source, high voltage source), switches, and a resonant circuit.

Dynamic magnetic focusing may be achieved for multi-energy acquisition modes when the voltage between the cathode and the anode (target) is rapidly changed between different values. The current through the focusing coil may be adjusted between a value for the lower-energy voltage and a value for the higher-energy voltage to maintain the geometry of the focal spot. In such embodiments, the electromagnet may be synchronized to the kV setting of the accelerating voltage to effectively maintain the geometry of the focal spot. The electromagnet may be controlled to determine the position of the focal spot.

Optionally, the focal spot may be moved using deflection magnets in addition to the electromagnet 326. The deflection magnets may also be electromagnets that are, for example, similarly positioned as the electrodes 228, 229 (FIG. 5). Current flowing through a coil that is wrapped about each deflection magnet may be controlled to modulate deflection of the electron beam. Compared to using focusing magnets alone, adjusting the position of the focal spot with deflection magnets may be easier to achieve, as the magnetic fields required for deflection are generally lower and do not need to be as accurate compared to those used for the focusing the beam. After focusing electronics are designed to maintain a focal spot geometry in kV switching using electromagnetic focusing, similar technology may be used to change the position of the focal spot as kV is switched.

Figure 11:
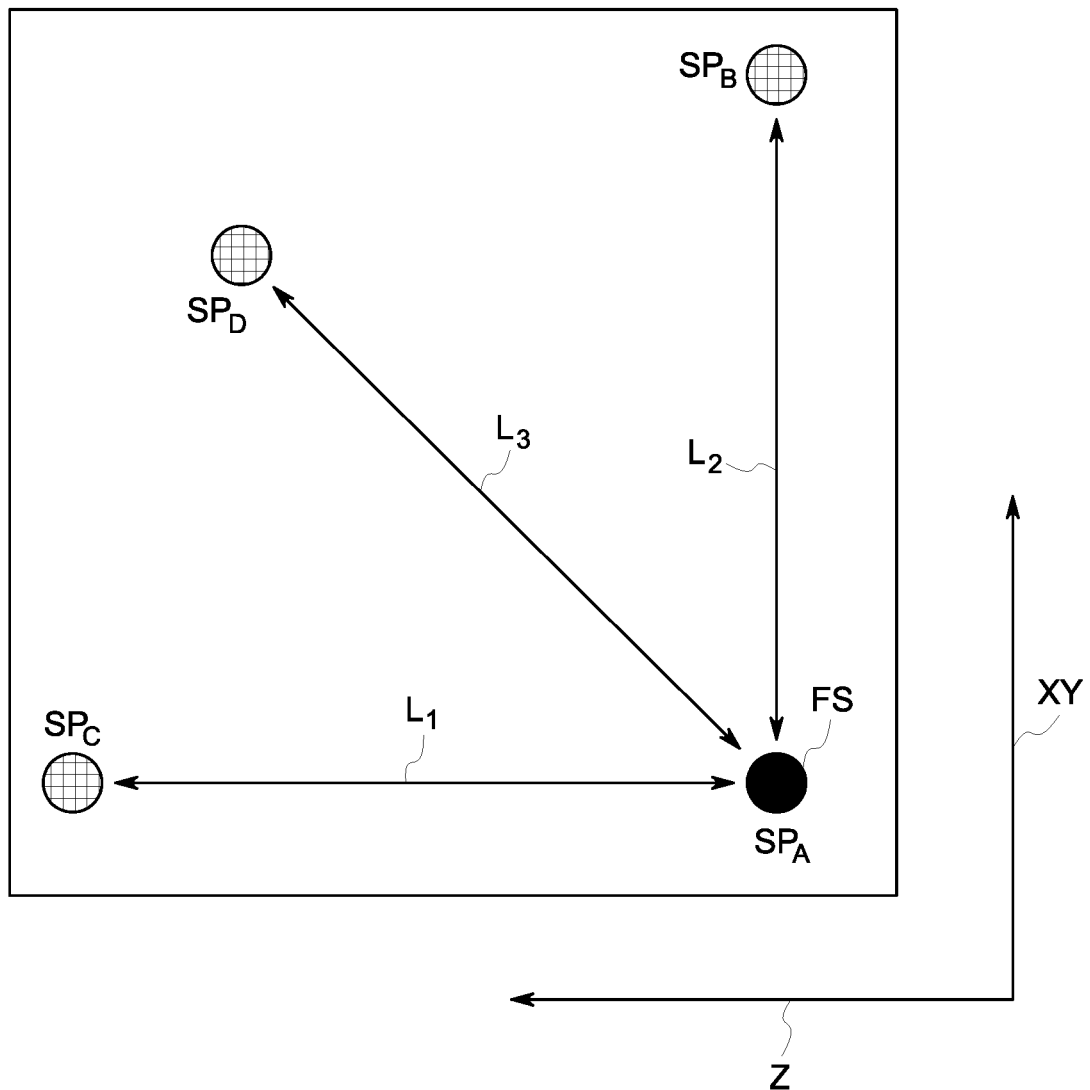
FIG. 11 illustrates how the focal spot may move axially, in-plane, or diagonally between different positions.

FIG. 11 illustrates how embodiments of the subject matter described herein may move a focal spot FS between different spot positions SP. As described wherein, the x-ray source may be operable to deflect (e.g., magnetically or electrostatically) by adjusting a strength of the respective field. For example, the focal spot FS may be moved in-plane (e.g., along the XY plane) between the spot position $SP_A$ and the spot position $SP_B$. The focal spot FS may be moved axially along the Z axis between the spot position $SP_A$ and the spot position $SP_C$. In certain embodiments, the focal spot FS may be moved diagonally such that the focal spot FS moves partially along the Z axis and partially along the XY plane between the spot position $SP_A$ and the spot position $SP_D$.

For embodiments that move the focal spot FS axially or in-plane, a distance between the different spot positions (e.g., SPA and SPB or SPA and SPC) may be about half the corresponding dimension of a detector pixel element. If the focal spot FS is moved in-plane along a width of the detector pixel elements, the distance between the spot positions SPA and SPB may be about half the width of a detector pixel element. If the focal spot FS is moved axially along a length of the detector pixel elements, the distance between the spot positions SPA and SPC may be about half the length of a detector pixel element. If the focal spot FS is moved diagonally, the distance between the spot positions SPA and SPD may be the length of a diagonal for a rectangle having one-half the length (L) of the detector pixel element and one-half the width (W) of the detector pixel element, which is the square root of $((0.5L)^2+(0.5W)^2)$. By way of example, a length and width of a detector pixel element may be 1.250 millimeter (mm)×1.250 mm. As another example, the length and width may be 1.000 mm×1.000 mm the length and width may be 0.625 mm×0.625 mm. The length and width may be 0.313 mm×0.313 mm, or the length and width may be 0.156 mm×0.156 mm. Although the above examples have the lengths and widths being equal, the lengths and widths may not be equal in other embodiments.

Pixel elements typically have a rectangular detection area. As used herein the phrase, "wherein the pixel elements have an area that is at least L mm X W mm" means that the length is at least L mm and the width is at least W mm. For example, the phrase "wherein the pixel elements have an area that is at least 0.156 mm×0.156 mm" means that the length is at least 0.156 mm and the width is at least 0.156 mm. In some embodiments, the pixel elements have an area that is at least 0.313 mm×0.313 mm. In certain embodiments, the pixel elements have an area that is at least 0.625 mm×0.625 mm. In particular embodiments, the pixel elements have an area that is at least 1.000 mm×1.000 mm.

As such, the spot position may move a greater distance when moving diagonally. Optionally, the diagonal movement may include unequal Z and XY components. For instance, the bi-directional arrow representing diagonal movement in FIG. 11 is about 45° with respect to the bi-directional arrows representing axial movement and in-plane movement. Optionally, the diagonal movement may be less than 45° or more than 45°.

Figure 7:
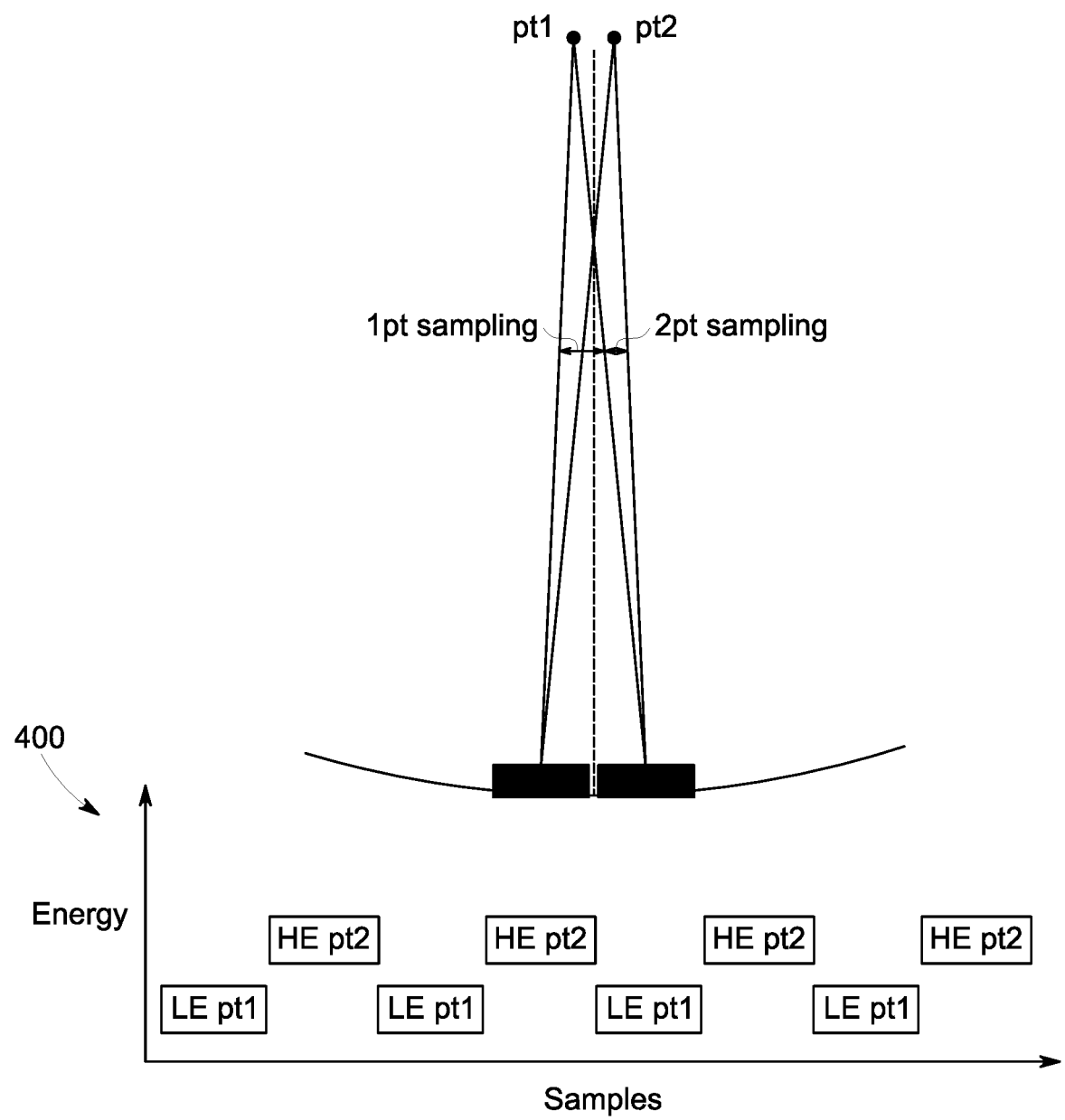
FIG. 7 illustrates a first acquisition mode in which attenuation data from different focal positions and at different energy levels may be acquired.
Figure 8:
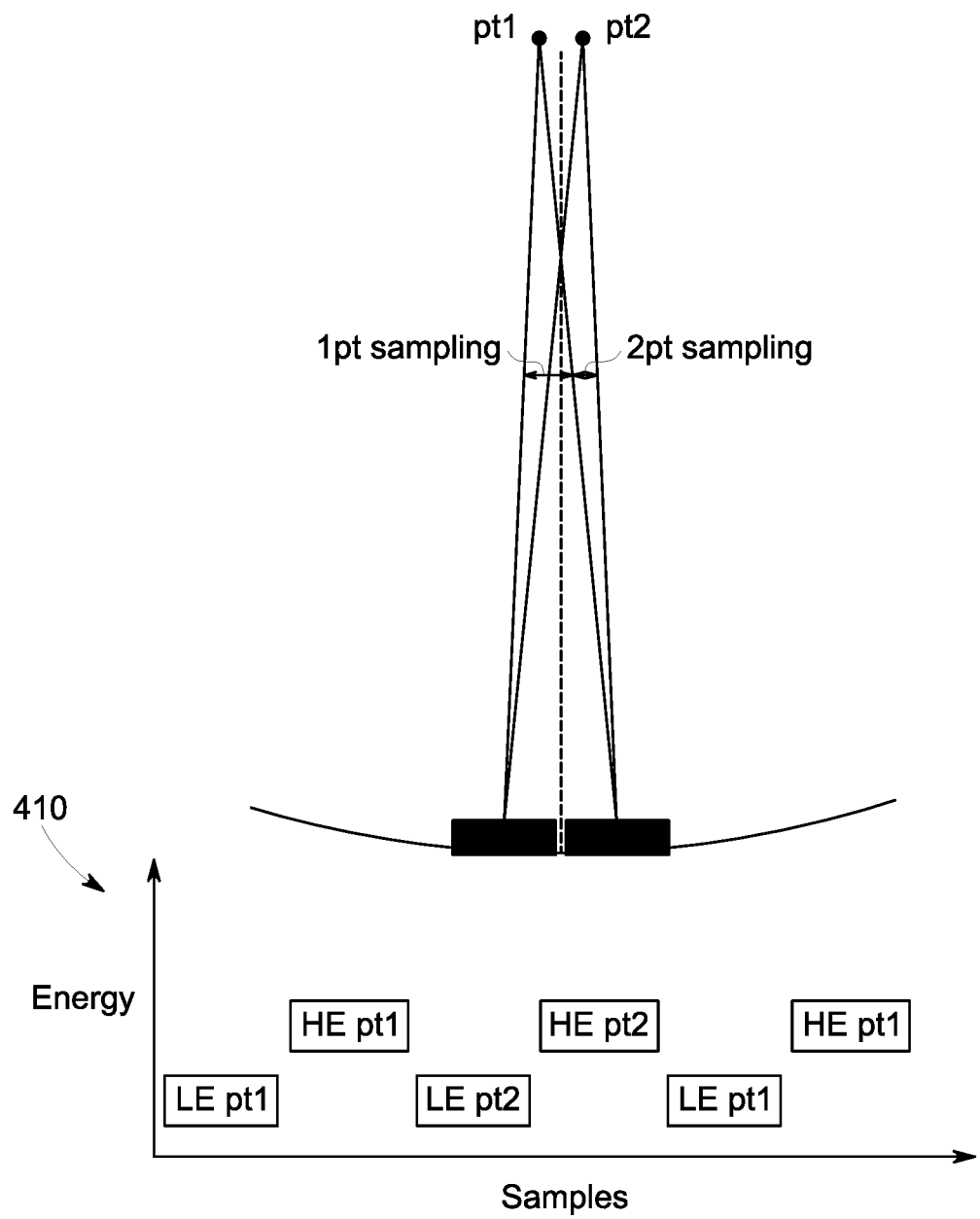
FIG. 8 illustrates a second acquisition mode in which attenuation data from different focal positions and at different energy levels may be obtained.

FIGS. 7 and 8 illustrate different acquisition modes that may utilize data acquired at different energy levels and different positions of the focal spot. In FIG. 7, the focal spot of the beam and the voltage of the power system may be controlled so that samples acquired at one energy level are acquired at the same position of the focal spot and samples acquired at another energy level are acquired at another position of the focal spot. As shown in the graph 400, each sample acquired at a low energy level (LE) is acquired at a first focal position (pt1) and each sample acquired at a high energy level (HE) is acquired at a second focal position (pt2). In such embodiments, the data may undergo interpolation to provide useful image data.

In FIG. 8, the focal spot of the beam and the voltage of the power system may be controlled so that subsequent samples acquired at one position of the focal spot are acquired at two energy levels. As shown in the graph 410, two samples are acquired at a first focal position (pt1), low energy (LE) followed by high energy (HE). Two following samples are then acquired at a second focal position (pt2), low energy (LE) followed by high energy (HE). Optionally, the two following samples may be acquired at the second focal position (pt2), high energy (HE) followed by low energy (LE). In other embodiments, the focal spot of the beam and the voltage of the power system may be controlled so that subsequent samples acquired at one energy level are acquired at different focal positions. For example, two samples are acquired at a high energy (HE), the first focal position (pt1) followed by the second focal position (pt2). Two following samples are then acquired at a low energy (LE), the first focal position (pt1) followed by the second focal position (pt2). Optionally, the two following samples may be acquired at a low energy (LE), the second focal position (pt2) followed by the first focal position (pt1).

Data acquired at different energy levels and focal positions may be processed to generate image data. A middle row 420 illustrates the acquired data, which includes low-energy data (hereinafter referred to as "lower-energy data") acquired at the focal spot having the first focal position and high-energy data (hereinafter referred to as "higher-energy data") acquired at the focal spot having the second focal position. The acquired data may then be separated to generate two sets of projections, a higher-energy projection and a lower-energy projection. The data is interpolated to provide the missing data, specifically, lower-energy data acquired at the focal spot having the second focal position and higher-energy data acquired at the focal spot having the first focal position. Interpolation may be performed in the projection-space or image-space.

Figure 9:
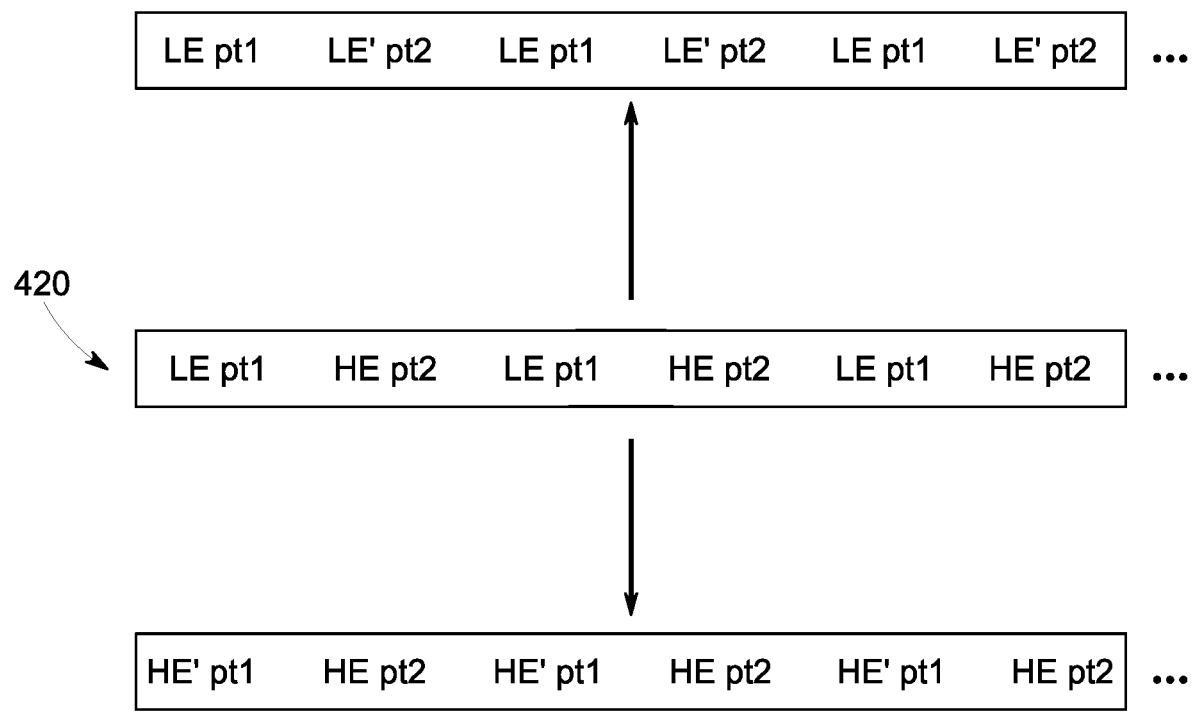
FIG. 9 illustrates image processing of the attenuation data from the first acquisition mode.

In FIG. 9, the data referenced as (LE' pt2) and (HE' pt1) refer to interpolated data. With acquired lower-energy data and interpolated higher-energy data corresponding to the first focal position, material density projections can be achieved through a material decomposition process to provide a first projection data set. Material decomposition is a process that is used to map projection data acquired at different energy levels to projection data that represents equivalent densities of the basis-material. Material decomposition differentiates materials (e.g., bone and tissue) in a person by decomposing the energy-dependent linear attenuation coefficients into a linear combination of energy-dependent basis functions and the corresponding basis set coefficients. Material density images may provide qualitative and quantitative information regarding tissue composition and contrast media distribution. Materials that may be imaged include, for example, iodine, water, calcium, hydroxyapatite (HAP), uric acid, and fat.

With interpolated lower-energy data and acquired higher-energy data corresponding to the second focal position, material density projections can also be achieved through a material decomposition process to provide a second projection data set. The first and second projection data sets may be reconstructed to provide high-resolution material-density (or spectral) image data.

In other embodiments, a lower-energy projection data set may be generated using the acquired lower-energy data corresponding to the first focal position and interpolated lower-energy data corresponding to the second focal position. A higher-energy projection data set may be generated using the acquired higher-energy data corresponding to the second focal position and interpolated higher-energy data corresponding to the first focal position. The higher-energy and lower-energy projection data sets may be reconstructed to provide higher-energy, high-resolution images and lower-energy, high-resolution images, respectively. With the high-resolution images at different energy levels, high-resolution material-density image data can be generated using image space material decomposition methods.

High-resolution monochromatic images at different energy levels can further be derived from the high-resolution material-density images. Accordingly, high-resolution material-density images may be generated in the projection domain or in the image domain.

Figure 10:
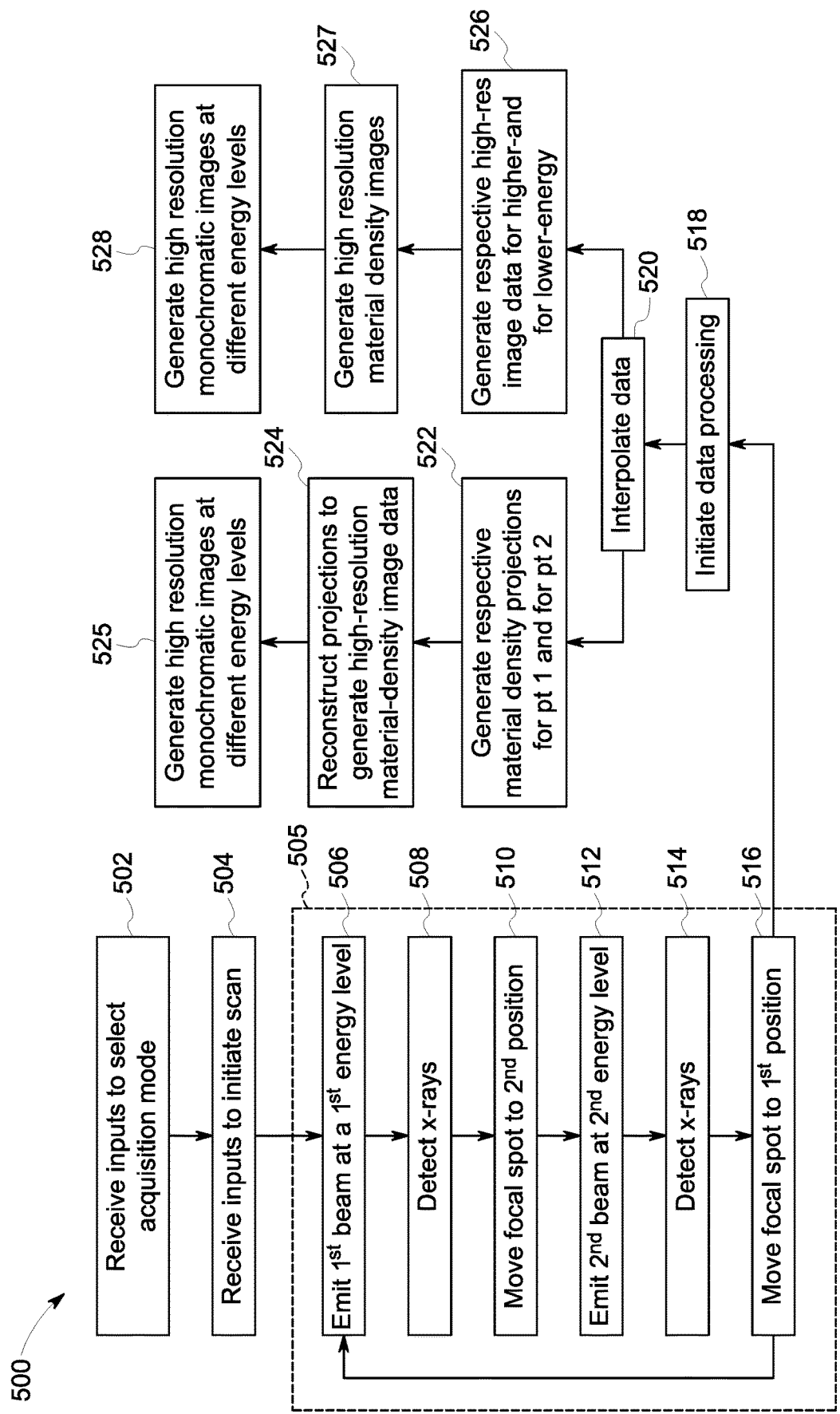
FIG. 10 is a flowchart illustrating a method of obtaining high-resolution image data having material-density information.

FIG. 10 is a flowchart illustrating a method 500 in accordance with an embodiment. The method 500 may be, for example, a method of obtaining high-resolution material-density image data. The method 500 employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. The method 500 may be carried out, at least in part, by the at least one processing unit 136 (FIG. 2).

The method 500 may include receiving operator inputs, at 502, to select an acquisition mode. The acquisition mode may be, for example, a high-resolution spectral imaging mode. In some embodiments, the operator inputs designated energy levels, such as a lower-energy level and a higher-energy level. Optionally, the operator inputs may designate one or more intermediate energy levels. In other embodiments, the acquisition mode selected by the operator may automatically populate or assign the energy levels.

At 504, the method 500 may include receiving operator inputs to initiate the scan. The scan may repeatedly execute an acquisition sub-sequence 505. The acquisition sub-sequence 505 includes emitting, at 506, a first beam of x-rays from a focal spot at a first designated energy level and detecting, at 508, the x-rays from the first beam after passing through the person. At 510, the focal spot may be moved to a different focal position (e.g., second focal position). The method 500 also includes emitting, at 512, a second beam of x-rays from a focal spot at a second designated energy level and detecting, at 514, the x-rays from the second beam after passing through the person. At 516, the focal spot may be moved to a different focal position (e.g., returned to the first focal position). The method 500 may repeat the acquisition sub-sequence 505 several times.

Accordingly, emission of the first and second beams may be synchronized with the first and second focal positions. In particular, the first beam may be provided when the focal spot is in the first focal position, and the second beam may be provided when the focal spot is in the second focal position. The CT system may not acquire attenuation data when the focal spot is in the first focal position and the beam has the second designated energy level. The CT system may not acquire attenuation data when the focal spot is in the second focal position and the beam has the first designated energy level.

In other embodiments, however, the acquisition sub-sequence 505 may have a different order of steps. For example, the sub-sequence may move the focal position prior to the second beam so that the acquired data for each view includes both energy levels. Alternatively, the sub-sequence may change the energy level while maintaining the focal position so that the acquired data for each view may include both energy levels.

At 518, data processing may be initiated. The data processing may be conducted in the projection domain and/or the image domain. At 520, the data may be interpolated, as described above, to fill in missing data points to complete data sets. For example, using the interpolated data, a higher-energy data set and a lower-energy data set for the first focal position may be formed and a higher-energy data set and a lower-energy data set for the second focal position may be formed. At 522, the high energy data set and low energy data set for each focal position may be processed to provide material density projections that may be used, in turn, to generate high-resolution material-density image data, at 524. Optionally, the high-resolution material-density image data may be processed, at 525, to generate high-resolution monochromatic images at different energy levels.

Alternatively, the data sets from step 520 may be used to generate higher-energy image data for each of the first and second focal positions and lower-energy image data for each of the first and second focal positions. The higher-energy data and lower-energy data may be reconstructed, at 526, to provide higher-energy high-resolution image data and lower-energy high-resolution image data, respectively. The image data from step 526 may be combined or fused, at 527, to generate high-resolution material-density image data. Optionally, the high-resolution material-density image data may be processed, at 528, to generate high-resolution monochromatic images at different energy levels.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements that do not have that property.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A computed tomography (CT) imaging system comprising:
    an x-ray source configured to be powered by a power system at different operating voltages, the x-ray source operable to emit a beam of x-rays from a focal spot toward an object, the x-ray source operable to move a spot position of the focal spot;
    a detector assembly configured to detect the x-rays attenuated by the object; and
    at least one processing unit configured to execute programmed instructions stored in memory, wherein the at least one processing unit, while executing the programmed instructions, is configured to:
- direct the x-ray source to emit different beams of the x-rays at different energy levels and to receive data from the detector assembly that are representative of detection of the x-rays emitted at the different energy levels;
- direct the x-ray source to move the focal spot between different spot positions such that the focal spot is at different spot positions while the beams are emitted at the different energy levels;
- receive higher-energy data from the detector assembly while the focal spot is in a first spot position and receive lower-energy data while the focal spot is in a second spot position;
- interpolate the higher-energy data at the second spot position and the lower-energy data at the first spot position;
- generate higher-energy high-resolution images using the higher-energy data for the first spot position and the higher-energy data for the second spot position;
- generate lower-energy high-resolution images using the lower-energy data for the first spot position and the lower-energy data for the second spot position; and
- reconstruct high-resolution material-density images using the higher-energy and lower-energy high-resolution images.

2. The CT imaging system of claim 1, wherein the at least one processing unit is configured to direct the x-ray source to, repeatedly:
- emit a first beam at a higher-energy level from the first spot position;
- move the focal spot toward the second spot position after emitting the first beam from the first spot position;
- emit a second beam at a lower-energy level from the second spot position; and
- move the focal spot toward the first spot position after emitting the second beam from the second spot position.

3. The CT imaging system of claim 1, wherein the beams are emitted along an XY plane that is perpendicular to a Z axis, the x-ray source moving the focal spot relative to the Z axis and relative to the XY plane.

4. The CT imaging system of claim 1, wherein the x-ray source includes electrodes that are spaced apart and positioned such that the beams of the x-rays pass between the electrodes, the electrodes operable to adjust a strength of an electric field between the electrodes to move the spot position of the focal spot.

5. The CT imaging system of claim 4, wherein the electrodes are configured to move the spot position between the first and second spot positions, the electric field being operable to deflect the different beams by differing amounts.

6. The CT imaging system of claim 1, wherein the x-ray source includes an electromagnet configured to generate a magnetic field, the electromagnet operable to adjust a strength of the magnetic field to move the spot position of the focal spot.

7. The CT imaging system of claim 1, wherein the at least one processing unit is configured to generate material density projections for two different materials for the first spot position of the focal spot using (a) a material decomposition process and (b) the lower-energy data for the first spot position of the focal spot and the higher-energy data for the first spot position of the focal spot;
wherein the at least one processing unit is configured to generate material density projections for the two different materials for the second spot position of the focal spot using (a) the material decomposition process and (b) the lower-energy data for the second spot position and the higher-energy data for the second spot position; and
wherein the at least one processing unit is configured to reconstruct the high-resolution material-density images using the material density projections for the two different materials from the first and second spot positions.

8. A method comprising:
- directing an x-ray source to emit different beams of x-rays at different energy levels;
- directing the x-ray source to move a focal spot of the x-ray source between different spot positions such that the focal spot is at different spot positions while the beams are emitted at the different energy levels,
  wherein directing the x-ray source to emit the different beams and to move the focal spot includes directing the x-ray source to repeating emit a first beam at a higher-energy level while the focal spot is in a first spot position, move the focal spot toward a different second spot position, emit a second beam having a lower-energy level while the focal spot is in the second spot position and move the focal spot toward the first spot position;
- receiving higher-energy data while the focal spot is in a first spot position and lower-energy data while the focal spot is in a second spot position;
- interpolating the higher-energy data at the second spot position and the lower-energy data at the first spot position;
- generating higher-energy high-resolution images using the higher-energy data for the first spot position and the higher-energy data for the second spot position;
- generating lower-energy high-resolution images using the lower-energy data for the first spot position and the lower-energy data for the second spot position; and
- reconstructing high-resolution images using the lower-energy data for the first spot position and the lower-energy data for the second spot position; and
- reconstruction high-resolution material-density images using the higher-energy and lower-energy high-resolution images.

9. The method of claim 8, wherein the beams are emitted along an XY plane that is perpendicular to a Z axis, the x-ray source moving the focal spot relative to the Z axis and relative to the XY plane while moving the focal spot between the different spot positions.

10. The method of claim 8, wherein the x-ray source includes electrodes that are spaced apart and positioned such that the beams of the x-rays pass between the electrodes, wherein moving the focal spot includes adjusting a strength of an electric field between the electrodes.

11. The method of claim 10, wherein adjusting the strength of the electric field causes the different beams to be deflected by differing amounts.

12. The method of claim 8, wherein the x-ray source includes an electromagnet configured to generate a magnetic field, wherein moving the focal spot includes adjusting a strength of the magnetic field of the electromagnet.

13. A computed tomography (CT) imaging system comprising:

an x-ray source configured to be powered by a power system at different operating voltages, the x-ray source operable to emit a beam of x-rays from a focal spot toward an object, the x-ray source operable to move a spot position of the focal spot;

a detector assembly configured to detect the x-rays attenuated by the object; and at least one processing unit configured to execute programmed instructions stored in memory, wherein the at least one processing unit, while executing the programmed instructions, is configured to:

direct the x-ray source to, repeatedly:

emit a first beam at a higher-energy level from a first spot position;

move the focal spot toward a second spot position after emitting the first beam from the first spot position;

emit a second beam at a lower-energy level from the second spot position; and move the focal spot toward the first spot position after emitting the second beam from the second spot position;

receive higher-energy data while the focal spot is in a first spot position and lower-energy data while the focal spot is in a second spot position;

interpolate the higher-energy data at the second spot position and the lower-energy data at the first spot position generate higher-energy high-resolution images using the higher-energy data for the first spot position and the higher-energy data for the second spot position;

generate lower-energy high resolution images using the lower-energy data for the first spot position and the lower-energy data for the second spot position; and reconstruct high-resolution material-density images using the higher-energy and lower-energy high resolution image.

14. The CT imaging system of claim 13, wherein the beams are emitted along an XY plane that is perpendicular to a Z axis, the x-ray source moving the focal spot relative to the Z axis and relative to the XY plane.

15. The CT imaging system of claim 13, wherein the x-ray source includes electrodes that are spaced apart and positioned such that the beams of the x-rays pass between the electrodes, the electrodes operable to adjust a strength of the electric field to move the spot position of the focal spot.

16. The CT imaging system of claim 13, wherein the detector assembly includes a plurality of detector pixel elements in which each detector pixel element of said plurality detects the x-rays emitted at higher energy levels and the x-rays emitted at lower energy levels.

* * * * *